United States Patent [19]

Häberle et al.

[11] Patent Number: 4,847,285
[45] Date of Patent: Jul. 11, 1989

[54] 1-SUBSTITUTED PHENYL-3-SUBSTITUTED METHYL-PYRROLIDINE-2,5-DIONES AND PLANT FUNGICIDE COMPOSITIONS CONTAINING SAME

[75] Inventors: Norman Häberle, Munich; Anneliese Reutter, Eglharting; Peter Kinzel, Westerham, all of Fed. Rep. of Germany

[73] Assignee: The Dow Chemical Company, Midland, Mich.

[21] Appl. No.: 186,549

[22] Filed: Apr. 27, 1988

Related U.S. Application Data

[63] Continuation of Ser. No. 757,900, Jul. 23, 1985, abandoned.

[30] Foreign Application Priority Data

Aug. 30, 1984 [DE] Fed. Rep. of Germany ....... 3431873

[51] Int. Cl.$^4$ .................... C07D 207/40; A01N 37/32
[52] U.S. Cl. .................................... 514/425; 548/547; 548/545
[58] Field of Search ................. 548/545, 547; 514/425

[56] References Cited

U.S. PATENT DOCUMENTS

| | | | |
|---|---|---|---|
| 3,538,114 | 11/1970 | Himmele et al. ............ | 548/565 |
| 3,586,697 | 6/1971 | Ozaki et al. ............ | 548/549 |

FOREIGN PATENT DOCUMENTS

| | | | |
|---|---|---|---|
| 0046274 | 2/1982 | European Pat. Off. ........... | 514/425 |
| 0173284 | 3/1986 | European Pat. Off. ........... | 548/545 |
| 0107137 | 8/1975 | Japan .................................. | 548/549 |
| 0007956 | 1/1977 | Japan .................................. | 514/425 |

*Primary Examiner*—David B. Springer
*Attorney, Agent, or Firm*—S. Preston Jones; Ronald G. Brookens

[57] ABSTRACT

Substituted 1-phenyl-3-methyl-pyrrolidinediones of the general formula:

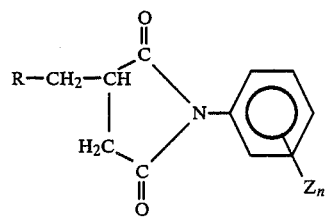

in which R may represent fluorine, chlorine, bromine, iodine, CN, SCN or methanesulfonyl, Z represents one or more of the same or different substituents selected from fluorine, chlorine, bromine, iodine, $NO_2$, CN, SCN, sulfamoyl, phenoxy, an alkyl having from 1 to 3 carbon atoms, a halogenalkyl having from 1 to 3 carbon atoms and 1 to 7 halogen atoms selected from fluorine, chlorine or bromine, an alkyloxy having from 1 to 3 carbon atoms, a halogenalkoxy having from 1 to 4 carbon atoms and 1 to 4 halogen atoms selected from the group consisting of fluorine, chlorine and bromine, an allyloxy or ethoxycarbonyl, and n is 0 or an integer from 1 to 4 with the following types of substitutions: 2-, 4-, 2,3-, 2,4-, 2,5-, 2,6-, 3,4-, 2,3,4-, 2,3,5-, 2,3,6-, 2,4,5-, 2,4,6-, 3,4,5-, 2,3,4,5-, 2,4,5,6- and 2,3,5,6-. The invention also relates to a process for making the compounds, which are active ingredients of fungicidal agents.

15 Claims, No Drawings

1-SUBSTITUTED PHENYL-3-SUBSTITUTED METHYL-PYRROLIDINE-2,5-DIONES AND PLANT FUNGICIDE COMPOSITIONS CONTAINING SAME

CROSS-REFERENCE TO RELATED APPLICATION

This is a continuation of application Ser. No. 757,900, filed July 23, 1985, abandoned.

The present invention relates to new 1-phenyl-3-methyl-pyrrolidine-2,5-diones, the substituent being at the methyl group, their preparation and application as fungicides.

1-Phenyl-3-methyl-pyrrolidine-2,5-diones and their fungicidal effectiveness, especially against *Botrytis cinerea*, are known. Recently, publications have appeared relating to phenomena of resistence with *Botrytis cinerea*, which were observed particularly in the 1-(3,5-dichlorophenyl)-pyrrolidinediones which were considered as being especially effective (See M. Grindle, Pestic. Sci. 12, 305, 1982).

Furthermore, according to Jap. Kokai No. 75/107.137 chloromethyl maleic acid anilides are known compounds which have the disadvantage of being chemically difficult to obtain, are instable under conditions of application and, further, have only a very narrow spectrum of effectiveness.

Accordingly, it is the object of the present invention to provide new fungicidal agents of greater effectiveness, which are stable when applied, i.e., when exposed to light, are easily obtained by chemical synthesis and are effective against toxic fungi, which are known to exhibit a resistance to dicarboxylanilides that are exclusively meta- or meta/meta'-substituted.

This and other related objects are achieved according to the present invention by compounds of the general formula:

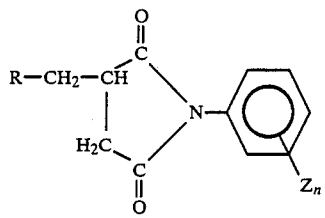

wherein,

R represents F, Cl, Br, I, CN, SCN or methanesulfonyl;
Z represents F, Cl, Br, I, $NO_2$, CN, SCN, sulfamoyl, phenoxy, an alkyl having from 1-3 carbon atoms, a halogenalkyl having from 1-3 carbon atoms and 1-7 halogen atoms from the group F, Cl and Br, an alkoxy having from 1-3 carbon atoms, a halogenalkoxy having from 1-3 carbon atoms and 1-4 halogen atoms from the group F, Cl and Br, an allyloxy and an ethoxycarbonyl; and
n is 0 or an integer of from 1 to 4 with the following types of substitutions: 2-, 4-, 2,3-, 2,4-, 2,5-, 2,6-, 3,4-, 2,3,4-, 2,3,5-, 2,3,6-, 2,4,5-, 2,4,6-, 3,4,5-, 2,3,4,5-, 2,4,5,6- or 2,3,5,6-.

Examples of alkyl groups for Z as defined above are methyl, ethyl, n-propyl and iso-propyl. Examples of halogenalkyl groups for Z according to the invention are trifluoromethyl, pentafluoroethyl, heptafluoropropyl, chloromethyl, dichloromethyl, trichloromethyl and bromomethyl. Examples of alkoxy groups for Z are methoxy, ethoxy and propoxy. Examples of halogenalkoxy groups for Z are, preferably, the difluoromethoxy and tetrafluoroethoxy groups.

Special examples for compounds according to the present invention are:

(1) 3-Chloromethyl-1-phenyl-pyrrolidine-2,5-dione
(2) 3-Chloromethyl-1-(4-fluorophenyl)-pyrrolidine-2,5-dione
(3) 3-Chloromethyl-1-(2-chlorophenyl)-pyrrolidine-2,5-dione
(4) 3-Chloromethyl-1-(4-chlorophenyl)-pyrrolidine-2,5-dione
(5) 3-Chloromethyl-1-(2-bromophenyl)-pyrrolidine-2,5-dione
(6) 3-Chloromethyl-1-(4-bromophenyl)-pyrrolidine-2,5-dione
(7) 3-Chloromethyl-1-(4-iodophenyl)-pyrrolidine-2,5-dione
(8) 3-Chloromethyl-1-(2,4-difluorophenyl)-pyrrolidine-2,5-dione
(9) 3-Chloromethyl-1-(2,6-difluorophenyl)-pyrrolidine-2,5-dione
(10) 3-Chloromethyl-1-(2,3-dichlorophenyl)-pyrrolidine-2,5-dione
(11) 3-Chloromethyl-1-(2,4-dichlorophenyl)-pyrrolidine-2,5-dione
(12) 3-Chloromethyl-1-(2,5-dichlorophenyl)-pyrrolidine-2,5-dione
(13) 3-Chloromethyl-1-(4-chloro-2-fluorophenyl)-pyrrolidine-2,5-dione
(14) 3-Chloromethyl-1-(2-chloro-4-fluorophenyl)-pyrrolidine-2,5-dione
(15) 3-Chloromethyl-1-(4-methylphenyl)-pyrrolidine-2,5-dione
(16) 3-Chloromethyl-1-(4-propylphenyl)-pyrrolidine-2,5-dione
(17) 3-Chloromethyl-1-(2,6-dimethylphenyl)-pyrrolidine-2,5-dione
(18) 3-Chloromethyl-1-(2,6-diethylphenyl)-pyrrolidine-2,5-dione
(19) 3-Chloromethyl-1-(5-fluoro-2-methylphenyl)-pyrrolidine-2,5-dione
(20) 3-Chloromethyl-1-(2-chloro-6-methylphenyl)-pyrrolidine-2,5-dione
(21) 3-Chloromethyl-1-(2-trifluoromethylphenyl)-pyrrolidine-2,5-dione
(22) 3-Fluoromethyl-1-(4-bromophenyl)-pyrrolidine-2,5-dione
(23) 3-Fluoromethyl-1-(4-iodophenyl)-pyrrolidine-2,5-dione
(24) 3-Fluoromethyl-1-(2,4-difluorophenyl)-pyrrolidine-2,5-dione
(25) 3-Fluoromethyl-1-(2,6-difluorophenyl)-pyrrolidine-2,5-dione
(26) 3-Fluoromethyl-1-(2,3-difluorophenyl)-pyrrolidine-2,5-dione
(27) 3-Fluoromethyl-1-(2,4-dichlorophenyl)-pyrrolidine-2,5-dione
(28) 3-Fluoromethyl-1-(2,5-dichlorophenyl)-pyrrolidine-2,5-dione
(29) 3-Fluoromethyl-1-(4-chloro-2-fluorophenyl)-pyrrolidine-2,5-dione
(30) 3-Fluoromethyl-1-(2-chloro-4-fluorophenyl)-pyrrolidine-2,5-dione
(31) 3-Fluoromethyl-1-(4-methylphenyl)-pyrrolidine-2,5-dione

(32) 3-Fluoromethyl-1-(4-propylphenyl)-pyrrolidine-2,5-dione
(33) 3-Fluoromethyl-1-(2,6-dimethylphenyl)-pyrrolidine-2,5-dione
(34) 3-Fluoromethyl-1-(2,6-diethylphenyl)-pyrrolidine-2,5-dione
(35) 3-Fluoromethyl-1-(5-fluoro-2-methylphenyl)-pyrrolidine-2,5-dione
(36) 3-Fluoromethyl-1-(2-chloro-6-methylphenyl)-pyrrolidine-2,5-dione
(37) 3-Fluoromethyl-1-(2-trifluoromethylphenyl)-pyrrolidine-2,5-dione
(38) 3-Chloromethyl-1-(4-trifluoromethylphenyl)-pyrrolidine-2,5-dione
(39) 3-Chloromethyl-1-(4-chloro-2-trifluoromethylphenyl)-pyrrolidine-2,5-dione
(40) 3-Chloromethyl-1-(4-methoxyphenyl)-pyrrolidine-2,5-dione
(41) 3-Chloromethyl-1-(4-allyloxyphenyl)-pyrrolidine-2,5-dione
(42) 3-Chloromethyl-1-(4-difluoromethoxyphenyl)-pyrrolidine-2,5-dione
(43) 3-Chloromethyl-1-[2-(1,1,2,2-tetrafluoroethoxy)-phenyl]-pyrrolidine-2,5-dione
(44) 3-Chloromethyl-1-[4-(1,1,2,2-tetrafluoroethoxy)-phenyl]-pyrrolidine-2,5-dione
(45) 3-Chloromethyl-1-[4-(2,3-dibromo)propoxyphenyl]-pyrrolidine-2,5-dione
(46) 3-Chloromethyl-1-(4-nitrophenyl)-pyrrolidine-2,5-dione
(47) 3-Chloromethyl-1-(4-fluoro-3-nitrophenyl)-pyrrolidine-2,5-dione
(48) 3-Chloromethyl-1-(4-phenoxyphenyl)-pyrrolidine-2,5-dione
(49) 3-Chloromethyl-1-(4-ethoxycarbonylphenyl)-pyrrolidine-2,5-dione
(50) 3-Chloromethyl-1-(4-cyanophenyl)-pyrrolidine-2,5-dione
(51) 3-Chloromethyl-1-(4-thiocyanatophenyl)-pyrrolidine-2,5-dione
(52) 3-Chloromethyl-1-(4-sulfamoylphenyl)-pyrrolidine-2,5-dione
(53) 3-Chloromethyl-1-(2,4-dimethylphenyl)-pyrrolidine-2,5-dione
(54) 3-Chloromethyl-1-(3-fluoro-2-methylphenyl)-pyrrolidine-2,5-dione
(55) 3-Chloromethyl-1-(4-fluoro-2-methylphenyl)-pyrrolidine-2,5-dione
(56) 3-Chloromethyl-1-(4-fluoro-3-methylphenyl)-pyrrolidine-2,5-dione
(57) 3-Chloromethyl-1-(4-chloro-2-methylphenyl)-pyrrolidine-2,5-dione
(58) 3-Chloromethyl-1-(4-bromo-2-methylphenyl)-pyrrolidine-2,5-dione
(59) 3-Chloromethyl-1-(4-bromo-3-methylphenyl)-pyrrolidine-2,5-dione
(60) 3-Chloromethyl-1-(2-methyl-4-nitrophenyl)-pyrrolidine-2,5-dione
(61) 3-Chloromethyl-1-(2-methyl-6-nitrophenyl)-pyrrolidine-2,5-dione
(62) 3-Chloromethyl-1-(2,4,6-trimethylphenyl)-pyrrolidine-2,5-dione
(63) 3-Chloromethyl-1-(4-bromo-2,6-dimethylphenyl)-pyrrolidine-2,5-dione
(64) 3-Chloromethyl-1-(2,4,6-trifluorophenyl)-pyrrolidine-2,5-dione
(65) 3-Chloromethyl-1-(2,3,5,6-tetrafluorophenyl)-pyrrolidine-2,5-dione
(66) 3-Chloromethyl-1-(2,4,5-trimethylphenyl)-pyrrolidine-2,5-dione
(67) 3-Fluoromethyl-1-(3-fluoro-2-methylphenyl)-pyrrolidine-2,5-dione
(68) 3-Fluoromethyl-1-(4-chloro-2-methylphenyl)-pyrrolidine-2,5-dione
(69) 3-Fluoromethyl-1-(4-bromo-2-methylphenyl)-pyrrolidine-2,5-dione
(70) 3-Fluoromethyl-1-(4-bromo-3-methylphenyl)-pyrrolidine-2,5-dione
(71) 3-Fluoromethyl-1-(2,4-dimethylphenyl)-pyrrolidine-2,5-dione
(72) 3-Fluoromethyl-1-(2-methyl-6-nitrophenyl)-pyrrolidine-2,5-dione
(73) 3-Bromomethyl-1-(4-fluorophenyl)-pyrrolidine-2,5-dione
(74) 3-Bromomethyl-1-(4-chlorophenyl)-pyrrolidine-2,5-dione
(75) 3-Bromomethyl-1-(2-fluorophenyl)-pyrrolidine-2,5-dione
(76) 3-Bromomethyl-1-(4-methylphenyl)-pyrrolidine-2,5-dione
(77) 3-Bromomethyl-1-(4-bromophenyl)-pyrrolidine-2,5-dione
(78) 3-Bromomethyl-1-(4-iodophenyl)-pyrrolidine-2,5-dione
(79) 3-Bromomethyl-1-(5-fluoro-2-methylphenyl)-pyrrolidine-2,5-dione
(80) 3-Bromomethyl-1-(2-chloro-5-trifluoromethylphenyl)-pyrrolidine-2,5-dione
(81) 3-Iodomethyl-1-(4-methylphenyl)-pyrrolidine-2,5-dione
(82) 3-Iodomethyl-1-phenyl-pyrrolidine-2,5-dione
(83) 3-Iodomethyl-1-(4-fluorophenyl)-pyrrolidine-2,5-dione
(84) 3-Iodomethyl-1-(4-chlorophenyl)-pyrrolidine-2,5-dione
(85) 3-Iodomethyl-1-(2,4-difluorophenyl)-pyrrolidine-2,5-dione
(87) 3-Iodomethyl-1-(2,3-dichlorophenyl)-pyrrolidine-2,5-dione
(88) 3-Iodomethyl-1-(2,4-dichlorophenyl)-pyrrolidine-2,5-dione
(89) 3-Iodomethyl-1-(2-trifluoromethylphenyl)-pyrrolidine-2,5-dione
(90) 3-Iodomethyl-1-(4-trifluoromethylphenyl)-pyrrolidine-2,5-dione
(91) 3-Iodomethyl-1-(4-allyloxyphenyl)-pyrrolidine-2,5-dione
(92) 3-Iodomethyl-1-(4-difluoromethoxyphenyl)-pyrrolidine-2,5-dione
(93) 3-Iodomethyl-1-[2-(1,1,2,2-tetrafluoroethoxy)-phenyl]-pyrrolidine-2,5-dione
(94) 3-Iodomethyl-1-[4-(1,1,2,2-tetrafluoroethoxy)-phenyl]-pyrrolidine-2,5-dione
(95) 3-Iodomethyl-1-(4-bromophenyl)-pyrrolidine-2,5-dione
(96) 3-Iodomethyl-1-(4-iodophenyl)-pyrrolidine-2,5-dione
(97) 3-Iodomethyl-1-(4-cyanophenyl)-pyrrolidine-2,5-dione
(98) 3-Iodomethyl-1-(4-fluoro-2-methylphenyl)-pyrrolidine-2,5-dione
(99) 3-Iodomethyl-1-(4-chloro-2-methylphenyl)-pyrrolidine-2,5-dione
(100) 3-Iodomethyl-1-(2,6-dimethylphenyl)-pyrrolidine-2,5-dione (101) 3-Iodomethyl-1-(2,4,5-trimethylphenyl)-pyrrolidine-2,5-dione
(102) 3-Iodomethyl-1-(2,4,6-trimethylphenyl)-pyrrolidine-2,5-dione
(103) 3-Iodomethyl-1-(2-chloro-4-sulfamoylphenyl)-pyrrolidine-2,5-dione
(104) 3-Iodomethyl-1-(2-fluoro-5-nitrophenyl)-pyrrolidine-2,5-dione
(105) 3-Iodomethyl-1-(2-methoxy-5-methylphenyl)-pyrrolidine-2,5-dione
(106) 3-Iodomethyl-1-(2,4,5-trichlorophenyl)-pyrrolidine-2,5-dione
(107) 3-Iodomethyl-1-(5-chloro-2-methylphenyl)-pyrrolidine-2,5-dione
(108) 3-Iodomethyl-1-(2-chloro-5-methylphenyl)-pyrrolidine-2,5-dione
(109) 3-Iodomethyl-1-(2-chloro-5-trifluoromethylphenyl)-pyrrolidine-2,5-dione
(110) 3-Iodomethyl-1-(4-chloro-3-fluoro-5-methylphenyl)-pyrrolidine-2,5-dione
(111) 3-Cyanomethyl-1-(4-fluorophenyl)-pyrrolidine-2,5-dione
(112) 3-Cyanomethyl-1-(2-fluoro-5-methylphenyl)-pyrrolidine-2,5-dione
(113) 3-Cyanomethyl-1-(4-chloro-3-fluoro-5-methylphenyl)-pyrrolidine-2,5-dione
(114) 3-Cyanomethyl-1-(2-chloro-5-trifluoromethylphenyl)-pyrrolidine-2,5-dione
(115) 3-Cyanomethyl-1-(2-chloro-5-methylphenyl)-pyrrolidine-2,5-dione
(116) 3-Cyanomethyl-1-(5-chloro-2-methylphenyl)-pyrrolidine-2,5-dione
(117) 3-Cyanomethyl-1-(2,4,5-trichlorophenyl)-pyrrolidine-2,5-dione
(118) 3-Cyanomethyl-1-(2-methoxy-5-methylphenyl)-pyrrolidine-2,5-dione
(119) 3-Cyanomethyl-1-(2-fluoro-5-nitrophenyl)-pyrrolidine-2,5-dione
(120) 3-Cyanomethyl-1-(2-chloro-4-sulfamoylphenyl)-pyrrolidine-2,5-dione
(121) 3-Cyanomethyl-1-(2,4,6-trimethylphenyl)-pyrrolidine-2,5-dione
(122) 3-Cyanomethyl-1-(2,4,5-trimethylphenyl)-pyrrolidine-2,5-dione
(123) 3-Thiocyanatomethyl-1-(4-fluorophenyl)-pyrrolidine-2,5-dione
(124) 3-Thiocyanatomethyl-1-(2-fluoro-5-methylphenyl)-pyrrolidine-2,5-dione
(125) 3-Thiocyanatomethyl-1-(4-chloro-3-fluoro-5-methylphenyl)-pyrrolidine-2,5-dione
(126) 3-Thiocyanatomethyl-1-(2-chloro-5-trifluoromethylphenyl)-pyrrolidine-2,5-dione
(127) 3-Thiocyanatomethyl-1-(2-chloro-5-methylphenyl)-pyrrolidine-2,5-dione
(128) 3-Thiocyanatomethyl-1-(5-chloro-2-methylphenyl)-pyrrolidine-2,5-dione
(129) 3-Thiocyanatomethyl-1-(2,4,5-trichlorophenyl)-pyrrolidine-2,5-dione
(130) 3-Thiocyanatomethyl-1-(2-methoxy-5-methylphenyl)-pyrrolidine-2,5-dione
(131) 3-Thiocyanatomethyl-1-(2-fluoro-5-nitrophenyl)-pyrrolidine-2,5-dione
(132) 3-Thiocyanatomethyl-1-(2-chloro-4-sulfamoylphenyl)-pyrrolidine-2,5-dione
(133) 3-Thiocyanatomethyl-1-(2,4,6-trimethylphenyl)-pyrrolidine-2,5-dione
(134) 3-Thiocyanatomethyl-1-(2,4,5-trimethylphenyl)-pyrrolidine-2,5-dione
(135) 3-Methanesulfonylmethyl-1-(4-fluorophenyl)-pyrrolidine-2,5-dione
(136) 3-Methanesulfonylmethyl-1-(2-fluoro-5-methylphenyl)-pyrrolidine-2,5-dione
(137) 3-Methanesulfonylmethyl-1-(4-chloro-3-fluoro-5-methylphenyl)-pyrrolidine-2,5-dione
(138) 3-Methanesulfonylmethyl-1-(2-chloro-5-trifluoromethylphenyl)-pyrrolidine-2,5-dione
(139) 3-Methanesulfonylmethyl-1-(2-chloro-5-methylphenyl)-pyrrolidine-2,5-dione
(140) 3-Methanesulfonylmethyl-1-(5-chloro-2-methylphenyl)-pyrrolidine-2,5-dione
(141) 3-Methanesulfonylmethyl-1-(2,4,5-trichlorophenyl)-pyrrolidine-2,5-dione
(142) 3-Methanesulfonylmethyl-1-(2-methoxy-5-methylphenyl)-pyrrolidine-2,5-dione
(143) 3-Methanesulfonylmethyl-1-(2-fluoro-5-nitrophenyl)-pyrrolidine-2,5-dione
(144) 3-Methanesulfonylmethyl-1-(2-chloro-4-sulfamoylphenyl)-pyrrolidine-2,5-dione
(145) 3-Methanesulfonylmethyl-1-(2,4,6-trimethylphenyl)-pyrrolidine-2,5-dione
(146) 3-Methanesulfonylmethyl-1-(2,4,5-trimethylphenyl)-pyrrolidine-2,5-dione
(147) 3-Fluoromethyl-1-(4-fluorophenyl)-pyrrolidine-2,5-dione
(148) 3-Fluoromethyl-1-(2-fluoro-5-methylphenyl)-pyrrolidine-2,5-dione
(149) 3-Fluoromethyl-1-(4-chloro-3-fluoro-5-methylphenyl)-pyrrolidine-2,5-dione
(150) 3-Fluoromethyl-1-(2-chloro-5-trifluoromethylphenyl)-pyrrolidine-2,5-dione
(151) 3-Fluoromethyl-1-(2-chloro-5-methylphenyl)-pyrrolidine-2,5-dione
(152) 3-Fluoromethyl-1-(5-chloro-2-methylphenyl)-pyrrolidine-2,5-dione
(153) 3-Fluoromethyl-1-(2,4,5-trichlorophenyl)-pyrrolidine-2,5-dione
(154) 3-Fluoromethyl-1-(2-methoxy-5-methylphenyl)-pyrrolidine-2,5-dione
(155) 3-Fluoromethyl-1-(2-fluoro-5-nitrophenyl)-pyrrolidine-2,5-dione
(156) 3-Fluoromethyl-1-(2-chloro-4 sulfamoylphenyl)-pyrrolidine-2,5-dione
(157) 3-Chloromethyl-1-(2,4-dibromophenyl)-pyrrolidine-2,5-dione
(158) 3-Chloromethyl-1-(2,6-dichlorophenyl)-pyrrolidine-2,5-dione
(159) 3-Bromomethyl-1-(5-bromo-2-methylphenyl)-pyrrolidine-2,5-dione
(160) 3-Bromomethyl-1-(4-chloro-2-fluoro-5-methylphenyl)-pyrrolidine-2,5-dione
(161) 3-Bromomethyl-1-(2-chloro-5-methylphenyl)-pyrrolidine-2,5-dione
(162) 3-Bromomethyl-1-(2,5-dichloro-4-methylphenyl)-pyrrolidine-2,5-dione
(163) 3-Bromomethyl-1-(5-chloro-2-methylphenyl)-pyrrolidine-2,5-dione
(164) 3-Bromomethyl-1-(2,5-dichlorophenyl)-pyrrolidine-2,5-dione
(165) 3-Bromomethyl-1-(2,3,4-trichlorophenyl)-pyrrolidine-2,5-dione
(166) 3-Bromomethyl-1-(2,4,5-trichlorophenyl)-pyrrolidine-2,5-dione
(167) 3-Bromomethyl-1-(4-cyanophenyl)-pyrrolidine-2,5-dione
(168) 3-Bromomethyl-1-(2,5-difluorophenyl)-pyrrolidine-2,5-dione (169) 3-Bromomethyl-1-(2-fluoro-5-methylphenyl)-pyrrolidine-2,5-dione
(170) 3-Bromomethyl-1-(2,4-difluoro-5-methylphenyl)-pyrrolidine-2,5-dione
(171) 3-Bromomethyl-1-(2-fluoro-5-nitrophenyl)-pyrrolidine-2,5-dione
(172) 3-Bromomethyl-1-(2-trifluoromethylphenyl)-pyrrolidine-2,5-dione
(173) 3-Bromomethyl-1-(4-trifluoromethylphenyl)-pyrrolidine-2,5-dione
(174) 3-Bromomethyl-1-(2-methoxy-5-methylphenyl)-pyrrolidine-2,5-dione
(175) 3-Bromomethyl-1-(3-methoxy-4-methylphenyl)-pyrrolidine-2,5-dione
(176) 3-Bromomethyl-1-(2-methoxy-5-methyl-4-nitrophenyl)-pyrrolidine-2,5-dione
(177) 3-Bromomethyl-1-(2,3-dimethyl-4-nitrophenyl)-pyrrolidine-2,5-dione
(178) 3-Bromomethyl-1-(4,5-dimethyl-2-nitrophenyl)-pyrrolidine-2,5-dione
(179) 3-Iodomethyl-1-(5-chloro-2-methylphenyl)-pyrrolidine-2,5-dione
(180) 3-Iodomethyl-1-(2-methyl-5-nitrophenyl)-pyrrolidine-2,5-dione
(181) 3-Bromomethyl-1-(5-chloro-2-methoxyphenyl)-pyrrolidine-2,5-dione Due to the assymetrical center of the 3-position of the 2,5-pyrrolidinediones, enantiomer formation results. The enantiomers of the invention are claimed singly and as a racemic mixture. The compounds according to the invention are obtainable by reaction of suitably substituted succinic acids, their chlorides or anhydrides, with appropriately substituted anilines.

A preferred process for preparing the compounds according to the present invention is characterized by the reaction of succinic acids, their chlorides or anhydrides, which are substituted in the 2-position by an
R—CH$_2$ group
wherein R represents F, Cl, Br, I, CN, SCN and methanesulfonyl, with anilines of the formula

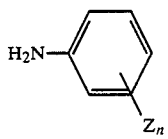

wherein
Z represents F, Cl, Br, I, NO$_2$, CN, SCN, sulfamoyl, phenoxy, an alkyl having from 1-3 carbon atoms, a halogenalkyl having from 1-3 carbon atoms and 1-7 halogen atoms from the group F, Cl and Br, an alkoxy having from 1-3 carbon atoms, a halogen-alkoxy having from 1-3 carbon atoms and 1-4 halogen atoms from the group F, Cl and Br, an allyloxy or ethoxycarbonyl; and
n is 0 or integer of from 1 to 4 with the following types of substitutions: 2-, 4-, 2,3-, 2,4-, 2,5-, 2,6-, 3,4-, 2,3,4-, 2,3,5-, 2,3,6-, 2,4,5-, 2,4,6-, 3,4,5-, 2,3,4,5-, 2,4,5,6- or 2,3,5,6-.

In the above types of substitution designated by n, the amine function of the aniline is always the 1-position of the phenyl group.

In a particularly advantageous variant of the process, the reaction of the succinic acid derivatives with the appropriate anilines is carried out in the presence of an inert solvent, e.g., xylene, with the reaction water formed being removed by azeotropic distillation. Tertiary amines, such as tributylamine or pyridine, among others, accelerate the splitting off of water Frequently, during the reaction of the succinic acid derivatives with the anilines there is a spontaneous formation of semi-anilides (by which such compounds are to be understood in which amide formation has already occurred, but not the ring formation to the corresponding imide). In a further advantageous variant of the process, these semi-anilides can be made to form the imide cycle by treatment with condensing agents, e g., toluene sulfonic acid, in a single-pot process In another alternative, the ring formation may be made to occur by azeotropic distillation of the reaction water, as already mentioned above.

Frequently, special examples of the compounds according to the present invention are prepared by first making the corresponding 3-halogen-(or pseudohalogens)-methyl-pyrrolidine-2,5-dione and, subsequently, the desired substituent R is introduced by conventional nucleophilic substitution.

The 3-halogen- or pseudohalogen-methyl-pyrrolidine-2,5-diones are available by addition of hydrogen halide or pseudohalide onto the corresponding imides of itaconic acid. The 3-bromomethyl-pyrrolidine-25-diones are available in a particularly advantageous process by ring formation of the corresponding itaconic anilides in the presence of acetyl bromide, with simultaneous ring formation to imide and hydrogen bromide addition at the methylene group of itaconic acid.

The succinic acid derivatives necessary as starting materials of the compounds according to the present invention are obtainable by known reactions with itaconic acid or itaconic acid derivatives. E.g., 2-chloromethylsuccinic acid anhydride is obtained by reaction of itaconic acid with thionylchloride in polar organic solvents. In an analogous manner, 2-bromomethylsuccinic acid anhydride by treatment with thionylbromide. Furthermore, 2-bromomethylsuccinic acid can be prepared by conventional means by addition of hydrogen bromide to itaconic acid. The other required substituted methylsuccinic acids are obtainable from the mentioned halogenmethylsuccinic acids by nucleophilic substitution at the halogenmethyl functional group. The methanesulfonyl group is advantageously obtained by oxidation of the corresponding methylthio- compound.

The anilines required for the preparation of the compounds according to the present invention, are commercially-available known compounds, otherwise prepared by known methods.

The compounds of the invention exhibit, as mentioned above, toxic properties against fungi and are useful on plants or plant products affected by fungi. They are, e.g., highly effective against all forms of *Botrytis cinerea* and accompanying fungi, such as *Alternaria solani*, and *Penicillium glaucum*. It is to be especially stressed that the inventive agents are effective even against those Botrytis strains which show resistance to known dicarboxylanilides.

Furthermore, such fungi are attacked as Alternaria types, Septoria types, *Verticillium dahliae*, Colletotrichum types, Monilia types, Fusarium types and Oomyceten, e g., *Pythium ultimum*. The compounds of the present invention are also effective against phytopathogenic fungi which adhere to the seeds, e.g., *Tilletia tritici*, *Fusarium nivale* and Helminthosporium types.

The inventive agents exhibit a broad spectrum of effectiveness. Thus, e.g., not only is Botrytis combated, but also the typically accompanying fungi. Consequently, with the agents according to the invention, the entire complex of fungi diseases can be treated and, therefore, the increased occurence of the accompanying fungi, which frequently is observed in the case of unbalanced treatment, can be avoided.

Some applications for the compounds of the present invention, without limitation thereto, are useful, e.g., in wine-growing, in horticulture, especially for salad plants, ornamental plants (alpine violets, geraniums), ornamental lawns, in the cultivation of rape, hops, strawberries and stone fruits.

Moreover, the pyrrolidine-2,5-diones of the present invention are useful for the conservation of harvested fruits. A further application of the compounds of the present invention is their use as seed-treatment agents. Additionally, the inventive compounds have a technical application as protective agents of wood and plastics.

The application of the effective agents is carried out by conventional means, e.g., by pouring, spraying, squirting, sprinkling, dusting and painting the area in which the fungi grow. Seed treatment may be carried out with dressing solutions. These treatments may have a prophylactic or curative effect.

The active compounds according to the present invention may be used alone or in combination with known pesticides specially fungicides. In general, they are to be used in combination with solid or liquid diluting agents or in solution with solid or liquid solvents, their amount being from 0.005 to 95% by weight. As a general rule, the mixtures are prepared as emulsion concentrates, pastes, spraying powders, granulates or micro capsules. In the following, all percentages are given by weight.

Emulsion concentrates and pastes contain usually 10–60%, preferably 15–50%, active compound, and 2–25% dispersing agent in organic solvents and/or water.

Spraying powders usually contain 10–80%, preferably 15–70%, active compound, 1–10% dispersing agents and 10–89% inert agents Granulates and dusting agents contain, in addition to inert components, binders and/or coating means, 1–10%, preferably 5–10%, active compound.

According to the present invention, the following compounds are useful as:

dispersing agents, e.g., alkyl- or aryl sulfonates, methyl cellulose, polymer sulfonic acids and their salts, polyalcohols, fatty acid esters, fatty alcohol ethers and fatty amines;

organic solvents, e.g., alcohols, e.g., ethanol and butanols, dimethylformamide, dimethylsulfoxide, N-methylpyrrolidone and aromatics, e.g., toluene and xylene;

inert components, e.g., kaolin, China-clay, talcum, calcium carbonate, highly dispersed silicic acid, silica gels, siliceous earth, diatomaceous earth, pumice, bruised corn, cyclodextrins; and thickening agents, e.g., starch and carboxymethyl cellulose; and binders, e g., magnesium sulfate, gypsum and gum arabic.

The fungicides according to the invention are, e.g., composed as follows:

1. Emulsion concentrate

20% by weight active agent
10% by weight commercial epoxidized anhydrosorbite monolaurate (trademark: "Tween-Twenty"); and
70% by weight dimethylformamide.

2. Spraying Powder

20% by weight active agents;
5% by weight Ammoniumlignin sulfonate (trademark: "Totanin");
10% by weight sodiumoleylmethyl tauride (trademark: "Arcopon T Konz") and
65% by weight kaolin.

The invention will now be more fully described by several examples. It should, however, be noted that such are given by way of illustration and not of limitation.

EXAMPLE 1

Preparation of 3-Chloromethyl-1-(4-fluorophenyl)-pyrrolidine-2,5-dione (a) To a solution of 130 g (1 mole) itaconic acid in 220 ml ethylacetate, 126 g (1.06 moles) thionyl chloride was added. The mixture was kept standing for 5 days at room temperature. The mixture was then heated to 80° C. until gas development ($SO_2$, HCl) ceased. Finally, the procedure was completed by distillation. Obtained were 140 g 2-chloromethylsuccinic acid anhydride, corresponding to 92% of the theoretical yield, having a boiling range of 118°–124° C. at 0.25 mbar.

(b) Into a solution of 33.3 g (0.3 moles) 4-fluoroaniline and a trace 4-toluene sulfonic acid in xylene, a xylene solution of 44.6 g (0.3 moles) 2-chloromethylsuccinic acid anhydride was added dropwise at room temperature while stirring. The temperature of the mixture rose to 40° C. during the operation. A suspension of the semi-anilide, which has a low solubility, was formed. After further stirring for 30 minutes and heating to a temperature whereby a reflux procedure can be carried out, the reaction water was azeotropically distilled off and drained over a water separator. After removal of 5 ml water, the liquid was cooled and the desired product was deposited in crystalline form and then recrystallized from toluene. The actual yield was 42% of the theoretical yield. The product had a melting point of 135° C.

(c) In a variant of (b), into a toluene solution of 33.3 g (0.3 moles) 4-fluoroaniline, a toluene solution of 44.6 g (0.3 moles) 2-chloromethylsuccinic acid anhydride were added dropwise at room temperature while stirring. The temperature of the mixture rose to 40° C. during the operation. To the suspension of the semi-anilide obtained, 0.35 moles of acetylchloride was added dropwise at 60° C. while stirring, the addition being carried out so slowly that the ensuing gas development could be easily controlled. After 3 hours the reaction mixture was heated to 100° C. and held at that temperature until the gas development was terminated. The semi-anilide thereby dissolved. When the reaction mixture was cooled down, the desired product crystallized. The actual yield was 93% of the theoretical yield.

EXAMPLE 2

Preparation of 3-Bromomethyl-1-(4-chlorophenyl)-pyrrolidine-2,5-dione (a) To a toluene solution of 33.6 g (0.3 moles) itaconic acid anhydride, a toluene solution of 50.1 g (0.3 moles) 4-chloroaniline was added dropwise while stirring. The reaction temperature of the reaction mixture was 40° C. A suspension of the corresponding semi-anilide was precipitated to which 28.1 g (0.36 moles) acetylchloride at 60° C. was added dropwise while stirring, the addition was carried out so slowly that a moderate gas development occurred. After 3 hours, the mixture was heated to 100° C. and the reaction mixture kept at this temperature until gas development stopped. After cooling the reaction mixture, 1-(4-chlorophenyl)-3-methylene-pyrrolidine-2,5-dione crystallized with a yield of 93% of the theoretical yield.

(b) To a chloroform solution having 41.8 g (0.25 moles) of the product obtained under (a), gaseous hydrogen bromide was introduced until the check of weight showed a 15%, by weight, excess of HBr. The mixture was stirred for 3 more hours at room temperature. After concentrating the solution, the desired product crystallized with a yield of 95% of the theoretical. Melting point: 134° C.

(c) In a further variant of the process, the itaconic acid semi-anilide obtained according to (a) was filtered off, washed with petroleum ether and dried. 46.3 g (0.25 moles) of the semi-anilide were suspended in acetic acid ethyl ester and, to the suspension, 33.8 g (0.27 moles) acetyl bromide were slowly added dropwise. Thereafter, the solution was refluxed for 4 hours, the solvent distilled off and the residue recrystallized from isopropanol/methanol. The desired product was obtained with a yield of 72% of the theoretical.

EXAMPLE 3

Preparation of
3-Iodomethyl-1-(4-fluorophenyl)-pyrrolidine-2,5-dione

A solution of 15.2 g (0.06 moles) 3-chloromethyl-1-(4-fluorophenyl)-pyrrolidine-2,5-dione (according to Example 1) and 10.7 g (0.066 moles) sodium iodide in acetone were refluxed for 8 hours in acetone. The precipitated sodium chloride was then filtered off, and the filtrate was concentrated, extracted with chloroform and the extract once more concentrated. The desired product was obtained in a yield of 92%. Melting point: 156° C.

EXAMPLE 4

Preparation of
3-Cyanomethyl-1-(4-fluorophenyl)-pyrrolidine-2,5-dione

A mixture was prepared of 48.3 g (0.2 moles) 3-chloromethyl-1-(4-fluorophenyl)-pyrrolidine-2,5-dione (according to Example 1), 300 ml methylene chloride and 7 g hexadecyltrimethylammonium chloride, dissolved in 80 ml water. To this mixture, a solution of 28.6 g (0.43 moles) potassium cyanide in 90 ml water was added dropwise at 0° C., and then stirred for 4 hours at 0° C. and another 12 hours at 20° C. The resulting phases were then separated with the organic phase being washed with water and dried with sodium sulfate. Finally, methylene chloride was distilled off and the residue dissolved in 250 ml toluene. Upon standing, the desired product crystallized. The actual yield was 44.1% of the theoretical yield. Melting point 97° C.

EXAMPLE 5

Preparation of
3-Thiocyanatomethyl-1-(4-fluorophenyl)-pyrrolidine-2,5-dione

The operation according to Example 4 was repeated with the difference being that instead of 0.43 moles potassium cyanide, 0.43 moles potassium thiocyanate were used. The desired product was obtained in a yield of 52% of the theoretical. Melting point: 88° C.

EXAMPLE 6

Preparation of
1-(4-fluorophenyl)-3-methanesulfonylmethyl-2,5-pyrrolidinedione (a) To a solution of 48.3 g (0.2 moles) 3-chloromethyl-1-(4-fluorophenyl)-2,5-pyrrolidinedione in 130 ml acetone, an ethanolic solution of 0.2 moles sodium methylmercaptide was added dropwise at 0° C. while stirring. After an additional 4 hours of stirring at 20° C. the salt formed was filtered off, the filtrate concentrated and the residue recrystallized from methanol. The desired product, 1-(4-fluorophenyl)-3-methylthiomethyl-2,5-pyrrolidinedione, was obtained in a yield of 70.3% of the theoretical yield.

(b) 12.5 g (0.05 moles) of the product obtained according to (a) were dissolved in 30 ml ethylacetate and after addition of 0.5 cc of a 0.1% ammonium molybdate solution, 0.36 ml concentrated acetic acid and 12 ml of a 10% aqueous sodium acetate solution, oxidized with 5 ml 60% solution of perhydrol were added while stirring at 50° C. For the completion of the reaction, heating at 80° C. was carried out while continuing to stir. Finally, the desired product was twice extracted from the mixture with 100 ml ethylacetate. Concentration of the mixture took place, during which the desired product was precipitated as a crystalline deposit. Yield: 63.7% of the theoretical. Melting range: 162°–163° C.

The following is a list of active compounds, designated by the letters A–F, according to the state of the art. (These compounds are similarly designated A–F in Tables 1, 3–5, 7 and 9). The active compounds according to the invention are designated, in the following tables, by the numerals provided on pages 2–12, supra.

A 3-Bromo-3-bromomethyl-1-(4-fluorophenyl)-2,5-pyrrolidinedione (corresponding to Jap. Kokai No. 77/38.021)

B 3-Chloro-1-(3,5-dichlorophenyl)-2,5-pyrrolidinedione (corresponding to GB-PS No. 14 62 140)

C 3-Chloro-1-(256-diethylphenyl)-2,5-pyrrolidinedione (corresponding to Jap. Kokai No. 75/125.743)

D 3,4-Dichloro-1-(4-fluorophenyl)-1-H-pyrrole-2,5-dione (corresponding to Jap. Kokai No. 71/2681)

E 3-Chloromethyl-1-(4-fluorophenyl)-1-H-pyrrole-2,5-dione (corresponding to Jap. Kokai No. 75/107.137)

F 4-Chlorophenyl)-3-methylene-2,5-pyrrolidinedione (corresponding to DE-OS No. 11 53 205)

EXAMPLE 7

Test for Stability to Light

In every instance, 1 mg of a substance to be tested, dissolved in a volatile solvent, was placed into an evaporating dish. After the solvent was evaporated, there remained a thin layer of the substance to be tested for stability to light. This layer was subsequently exposed to an irradiating lamp, the range of radiation of which corresponded to the light of the sun (xenon radiator with filtering system; range of wavelength 300 to 830 nm). In all cases, the half-life periods of the tested substances were determined under constant radiation conditions. The analysis was made by means of high pressure liquid chromatography.

TABLE 1

| Active Compound | Half-Life Period (Minutes) |
|---|---|
| 2 | 240 |
| 4 | 890 |
| 17 | 310 |
| 83 | 740 |
| E | 23 |

EXAMPLE 8

Spore-Germination Test 50 ul of a solution or suspension containing 250 ppm or 16 ppm, respectively, of active substance were introduced together with 50 ul of a spore suspension into hollow ground slides. The spore suspension was prepared by rinsing spores off an agar culture by means of a nutrient solution which contained, per liter, 10 g sugar, 1 g glycol, 1 g $KH_2PO_4$ and 0.5 g $MgSO_4$. The slides were kept for 48 hours at 20° C. in a Petri dish, the bottom of which was covered with moistened filtering paper. Thereafter the ratio of the germinated and ungerminated spores was compared with an untreated control specimen.

The degree of effectiveness is indicated in percentages calculated according to the following formula $$100 - \frac{\text{number of germinated spores, treated}}{\text{number of germinated spores, untreated}} \times 100$$

The results are shown in Tables 2 and 3.

TABLE NO. 2

TOXICITY AGAINST FUNGI OF THE 2,5-PYRROLIDINEDIONES ACCORDING TO THE INVENTION AT 250 PPM CONCENTRATION OF ACTIVE COMPOUND IN %

| Active Compound | Alternaria solani | Botrytis cinerea | Fusarium culmorum | Fusarium nivale | Colletotrichium coffeanum | Verticillium dahliae | Penicillium glaucum |
|---|---|---|---|---|---|---|---|
| 1 | 100 | 70 | 70 | 80 | 80 | 100 | 50 |
| 2 | 100 | 100 | 100 | 100 | 100 | 100 | 100 |
| 3 | 80 | 100 | 80 | 100 | 100 | 100 | 80 |
| 4 | 100 | 80 | 100 | 100 | 100 | 100 | 80 |
| 6 | 80 | 70 | 100 | 100 | 100 | 100 | 80 |
| 7 | 70 | 70 | 100 | 100 | 100 | 100 | 80 |
| 8 | 100 | 100 | 100 | 100 | 100 | 100 | 100 |
| 9 | 100 | 100 | 80 | 100 | 100 | 100 | 100 |
| 10 | 100 | 100 | 100 | 100 | 100 | 100 | 100 |
| 11 | 100 | 100 | 100 | 100 | 100 | 100 | 100 |
| 12 | 100 | 100 | 100 | 100 | 100 | 100 | 100 |
| 13 | 100 | 100 | 100 | 100 | 100 | 100 | 100 |
| 14 | 100 | 100 | 100 | 100 | 100 | 100 | 100 |
| 16 | 80 | 50 | 70 | 100 | 100 | 100 | 60 |
| 19 | 100 | 100 | 60 | 100 | 100 | 100 | 80 |
| 20 | 80 | 100 | 80 | 100 | 100 | 100 | 100 |
| 38 | 100 | 100 | 80 | 100 | 100 | 100 | 80 |
| 40 | 100 | 70 | 70 | 100 | 100 | 100 | 80 |
| 41 | 100 | 60 | 100 | 100 | 100 | 100 | 100 |
| 42 | 100 | 100 | 100 | 100 | 80 | 100 | 80 |
| 46 | 90 | 100 | 80 | 100 | 100 | 100 | 100 |
| 47 | 100 | 100 | 80 | 100 | 100 | 100 | 80 |
| 48 | 80 | 60 | 20 | 100 | 100 | 80 | 70 |
| 49 | 80 | 90 | 100 | 100 | 100 | 100 | 100 |
| 73 | 90 | 100 | 90 | 100 | 100 | 100 | 100 |
| 74 | 100 | 100 | 100 | 100 | 100 | 100 | 100 |
| 82 | 100 | 100 | 100 | 100 | 90 | 100 | 80 |
| 83 | 100 | 100 | 100 | 100 | 100 | 100 | 100 |
| 84 | 100 | 100 | 100 | 100 | 100 | 100 | 100 |
| 85 | 100 | 100 | 100 | 100 | 100 | 100 | 100 |
| 86 | 100 | 100 | 100 | 100 | 100 | 100 | 80 |
| 87 | 100 | 100 | 100 | 100 | 100 | 100 | 100 |
| 88 | 100 | 100 | 100 | 100 | 100 | 100 | 100 |
| 90 | 70 | 100 | 100 | 100 | 100 | 100 | 100 |
| 91 | 100 | 100 | 100 | 100 | 100 | 100 | 100 |
| 92 | 100 | 100 | 100 | 100 | 100 | 100 | 100 |
| 94 | 90 | 100 | 90 | 100 | 100 | 100 | 100 |
| 100 | 80 | 70 | 60 | 100 | 100 | 100 | 70 |
| 123 | 100 | 100 | 100 | 100 | 100 | 100 | 100 |
| 135 | 80 | 60 | 60 | 100 | 100 | 100 | 80 |

TABLE NO. 3

TOXICITY AGAINST FUNGI OF THE 2,5-PYRROLIDINEDIONES ACCORDING TO THE INVENTION AND OF COMPARISON SUBSTANCES AT 16 PPM CONCENTRATION OF ACTIVE COMPOUND IN %

| Active Compound | Alternaria solani | Botrytis cinerea | Fusarium culmorum | Fusarium nivale | Colletotrichium coffeanum | Verticillium dahliae | Penicillium glaucum |
|---|---|---|---|---|---|---|---|
| 4 | 100 | 60 | 70 | 100 | 100 | 40 | 60 |
| 7 | 50 | 50 | 70 | 100 | 100 | 50 | 50 |
| 8 | 80 | 80 | 80 | 100 | 80 | 100 | 80 |
| 10 | 80 | 50 | 0 | 100 | 80 | 60 | 80 |
| 13 | 100 | 80 | 40 | 80 | 100 | 80 | 90 |
| 38 | 60 | 70 | 40 | 80 | 100 | 80 | 40 |
| 47 | 100 | 100 | 60 | 40 | 100 | 50 | 40 |
| 74 | 40 | 80 | 40 | 100 | 100 | 100 | 60 |

TABLE NO. 3-continued

TOXICITY AGAINST FUNGI OF THE 2,5-PYRROLIDINEDIONES
ACCORDING TO THE INVENTION AND OF COMPARISON
SUBSTANCES AT 16 PPM CONCENTRATION
OF ACTIVE COMPOUND IN %

| Active Compound | Alternaria solani | Botrytis cinerea | Fusarium culmorum | Fusarium nivale | Colletotrichium coffeanum | Verticillium dahliae | Penicillium glaucum |
|---|---|---|---|---|---|---|---|
| 84 | 100 | 60 | 60 | 100 | 100 | 60 | 40 |
| 87 | 100 | 60 | 0 | 100 | 60 | 80 | 100 |
| A | 0 | 0 | 0 | 0 | 10 | 10 | 0 |
| B | 60 | 40 | 0 | 80 | 80 | 60 | 60 |
| C | 40 | 60 | 60 | 80 | 80 | 60 | 40 |
| D | 50 | 70 | 30 | 30 | 90 | 90 | 30 |

Upon comparison of the results in Table 3 between the compounds of the present invention and those considered state of the art, it becomes evident that the 2,5-pyrrolidinediones of the invention have superior toxicity against fungi and, especially, a considerably broader spectrum of activity. The compared substances exhibit, in all cases, the same or similar structural elements. This leads to the conclusion that the superior toxicity against fungi of the substances according to the present invention must be derived from the selection of the substituents on the succinic acid imide frame.

EXAMPLE 9

Seed Dressing Test Effectiveness Against *Helminthosporium gramineum*

Naturally infected barley seed underwent dressing treatment with the active compounds listed in the following Table and was subsequently placed into dishes containing a mixture of peat and sand, the thickness of the covering layer of the mixture being 2.5 cm. The dishes were closed and remained for 2 weeks in a darkened heat-conditioned cupboard at a temperature of 3°-6° C. The lids were then removed and the dishes kept for an additional two weeks at daylight at 20° C. under hot-house conditions. The plants which had grown were tested for impairment. The number of sick or damaged plants was established and compared with untreated controls. The results are shown in Table 4:

TABLE NO. 4

EFFECTVENESS IN % OF SUBSTANCES ACCORDING
TO THE INVENTION AND COMPARISON COMPOUNDS
AT 500 PPM CONCENTRATION OF ACTIVE COMPOUND
AGAINST *Helminthosporium gramineum*

| Agent Number | Effectiveness % |
|---|---|
| 3 | 70 |
| 4 | 90 |
| 14 | 80 |
| 15 | 80 |
| 19 | 70 |
| 39 | 70 |
| 40 | 70 |
| 42 | 70 |
| 62 | 100 |
| 74 | 90 |
| 82 | 90 |
| 83 | 90 |
| 84 | 90 |
| 85 | 80 |
| 86 | 100 |
| 89 | 70 |
| 92 | 80 |
| 94 | 80 |
| A | 40 |
| B | 35 |
| C | 15 |
| D | 50 |
| E | 15 |

EXAMPLE 10

Grape Juice Test 20 ml of a nutrient solution of grape juice and distilled water in the ratio 1:1 were poured into Petri dishes and thereto were added the active compounds listed in the following Table. The concentration of the active compounds was 31 ppm. Subsequently, in every case, the test specimens were inoculated with 50 ul of a Botrytis-spore suspension, made by rinsing off the Botrytis spores from an agar culture with distilled water.

After an incubating time of 10 or 20 days at 20° C. the amount of fungus development on the surface of the nutrient solution was evaluated.

The degree of efficiency was calculated in percent according to the following formula:

$$100 - \frac{\text{Fungus Growth, treated}}{\text{Fungus Growth, untreated}} \times 100$$

TABLE NO. 5

EFFECTIVENESS IN % OF 2,5-PYRROLIDINEDIONES
ACCORDING TO THE INVENTION AND COMPARISON
COMPOUNDS AT 31 PPM ACTIVE COMPOUND CONCENTRATION AFTER 10 AND 20 DAYS, RESPECTIVELY

| Effective Active Compound | % Effectiveness After 10 days | % Effectivenes After 20 days |
|---|---|---|
| 2 | 100 | 90 |
| 3 | 100 | 100 |
| 12 | 100 | 90 |
| 39 | 100 | 80 |
| 74 | 100 | 80 |
| 83 | 100 | 100 |
| 84 | 100 | 100 |
| 85 | 100 | 90 |
| 86 | 100 | 100 |
| 87 | 100 | 100 |
| 88 | 100 | 100 |
| 90 | 100 | 100 |
| 92 | 100 | 100 |
| 94 | 100 | 100 |
| 123 | 100 | 80 |
| B | 40 | 10 |
| D | 80 | 60 |

EXAMPLE 11

Grape Juice With Resistant *Botrytis cinerea* Strains

The operation of Example 10 was repeated with the difference being that the inoculation took place with spores of *Botrytis cinerea*, which are resistant to N-(3,5-dichlorophenyl)-imide. The effective concentration was 62 ppm.

As comparison agent "Ronilan" (a registered trademark of BASF), which is 3-(3,5-dichlorophenyl)-5-ethenyl-5-methyl-2,4-oxazolidinedione, was employed. The incubation time was 20 days. The results are shown in Table 6.

TABLE NO. 6
EFFECTIVENESS OF THE INVENTIVE 2,5-PYRROLIDINEDIONES AND THE COMPARISON AGENT IN %

| Effective Agent | Sensitive Strain | Resistant Strain A | Resistant Strain B |
|---|---|---|---|
| 73 | 100 | 100 | 100 |
| 74 | 100 | 100 | 100 |
| 83 | 100 | 100 | 100 |
| 90 | 100 | 100 | 100 |
| Ronilan | 90 | 30 | 30 |

EXAMPLE 12

Botrytis Test on Live Bean Plants

Young bean plants already showing the first three-foliated shoots, were sprayed with a solution containing 500 ppm active compound concentration, until the plants in the pots were visibly wet. After the spraying wetness was off, the bean plants were artificially infected by spraying with a *Botrytis cinerea*-spore suspension. The thus treated plants were stored at 20° C. and 95% relative humidity in air for 6 days and then evaluated for infection. Untreated plants served as the control.

TABLE NO. 7
EFFECTIVENESS IN % OF 2,5-PYRROLIDINEDIONES ACCORDING TO THE INVENTION AND OF COMPARISON SUBSTANCES AGAINST *Botrytis cinerea* ON BEAN PLANTS WITH 500 PPM ACTIVE COMPOUND CONCENTRATION

| Effective Agent | Effectiveness in % |
|---|---|
| 1 | 90 |
| 2 | 90 |
| 4 | 70 |
| 5 | 75 |
| 6 | 75 |
| 7 | 85 |
| 8 | 80 |
| 12 | 80 |
| 38 | 70 |
| 46 | 80 |
| 47 | 70 |
| 73 | 70 |
| 74 | 80 |
| 82 | 70 |
| 83 | 80 |
| Active Compound | |
| 84 | 70 |
| 85 | 85 |
| 87 | 80 |
| 90 | 95 |
| 91 | 70 |
| 92 | 75 |
| 94 | 80 |
| 123 | 70 |
| A | 60 |
| B | 60 |
| D | 30 |

EXAMPLE 13

Botrytis Test on Live Bean Plants with Resistant *Botrytis cinerea* Strains

The procedure of Example 12 was repeated with the difference being that the infection which was brought about showed resistance against N-(3,5-dichlorophenyl)-imides.

As comparison agents such substances as generally known to the art were used. These were "Ronilan" and "Rovral" (3-(3,5-dichlorophenyl)-N-(1-methylethyl)-2,4-dioxo-1-imidazolidinecarboxylamide).

TABLE NO. 8
FUNGI TOXICITY EFFECTIVENESS IN % OF 2,5-PYRROLIDINEDIONES ACCORDING TO THE PRESENT INVENTION AND COMPARISON SUBSTANCES AGAINST RESISTANT Botrytis STRAINS AT 500 PPM ACTIVE COMPOUND CONCENTRATION

| Active Compound | Sensitive Strain | Resistant Strain A | Resistant Strain B |
|---|---|---|---|
| 2 | 90 | 85 | 90 |
| 73 | 70 | 80 | 70 |
| 74 | 80 | 80 | 70 |
| 83 | 80 | 80 | 75 |
| 90 | 90 | 80 | 90 |
| Ronilan* | 85 | 25 | 45 |
| Rovral** | 87 | 20 | 40 |

*Ronilan is a registered trademark of BASF
**Rovral is a registered trademark of Rhone-Poulenc SA

EXAMPLE 14

Effectiveness Against *Pythium ultimum* in Soil Application

The active compounds listed in Table 9 (concentration of 500 ppm active ingredient), were mixed uniformly with soil that was artificially infected with *Pythium ultimum*. The thus treated soil was filled into plastic pots (4 repetitions per test substance) and each pot seeded with 10 pea seeds. These pots were stored for 10 days at 24°-26° C. and at a relative humidity of 75-90%. The number of grown healthy plants was then determined. The degree of effectiveness was calculated by comparison with infected, but untreated soil specimens. The following Table shows the results:

TABLE NO. 9
EFFECTIVENESS OF 2,5-PYRROLIDINEDIONES AND OF COMPARISON SUBSTANCES IN % AGAINST *Pythium ultimum*, AT A CONCENTRATION OF ACTIVE COMPOUND OF 500 PPM

| Active Compound | % Effectiveness |
|---|---|
| 3 | 80 |
| 4 | 100 |
| 5 | 100 |
| 8 | 100 |
| 9 | 100 |
| 15 | 100 |
| 17 | 80 |
| 19 | 100 |
| 20 | 85 |
| 40 | 100 |
| 46 | 100 |
| 73 | 100 |
| 74 | 100 |
| 85 | 100 |
| 86 | 100 |
| 123 | 100 |
| A | 40 |
| B | 0 |
| D | 0 |
| E | 50 |

While only several embodiments and examples of the present invention have been shown and described, it is obvious that many changes and modifications may be made thereunto, without departing from the spirit and scope of the invention.

What is claimed is:

1. A compound of the formula

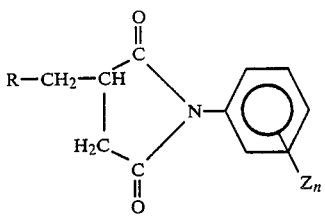

wherein
  R represents a member selected from the group consisting of fluorine, chlorine, bromine, iodine, CN, SCN and methanesulfonyl;
  Z represents one or more of the same or different substituents independently selected from the group consisting of fluorine, chlorine, bromine, iodine, $NO_2$, CN, SCN, sulfamoyl, phenoxy, an alkyl having from 1 to 3 carbon atoms, a halogenalkyl having from 1 to 3 carbon atoms and 1 to 7 halogen atoms selected from the group consisting of fluorine, chlorine and bromine, an alkoxy having from 1 to 3 carbon atoms, a halogenalkoxy having from 1 to 3 carbon atoms and 1 to 4 halogen atoms selected from the group consisting of fluorine, chlorine and bromine, an allyloxy and ethoxycarbonyl; and
  n is 0 or an integer from 1 to 4 with a type of substitution selected from the group consisting of 2-, 4-, 2,3-, 2,4-, 2,5-, 2,6-, 3,4-, 2,3,4-, 2,3,5-, 2,3,6-, 2,4,5-, 2,4,6-, 3,4,5-, 2,3,4,5-, 2,4,5,6- and 2,3,5,6-.

2. The compound according to claim 1, wherein said halogenalkoxy group for Z is a member selected from the group consisting of difluoromethoxy and tetrafluoroethoxy.

3. A fungicidal composition, comprising an effective amount of at least one active agent of the formula:

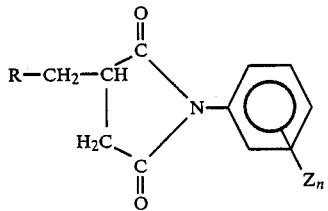

wherein
  R represents a member selected from the group consisting of fluorine, chlorine, bromine, iodine, CN, SCN and methanesulfonyl;
  Z represents one or more of the same or different substituents independently selected from the group consisting of fluorine, chlorine, bromine, iodine, $NO_2$, CN, SCN, sulfamoyl, phenoxy, an alkyl having from 1 to 3 carbon atoms, a halogenalkyl having from to 3 carbon atoms and 1 to 7 halogen atoms selected from the group consisting of fluorine, chlorine and bromine, an alkoxy having from 1 to 3 carbon atoms, a halogenalkoxy having from 1 to 3 carbon atoms and 1 to 4 halogen atoms selected from the group consisting of fluorine, chlorine and bromine, an allyloxy and ethoxycarbonyl; and
  n is 0 or an integer from 1 to 4 with a type of substitution selected from the group consisting of 2-, 4-, 2,3-, 2,4-, 2,5-, 2,6-, 3,4-, 2,3,4-, 2,3,5-, 2,3,6-, 2,4,5-, 2,4,6-, 3,4,5-, 2,3,4,5-, 2,4,5,6- and 2,3,5,6-.

4. The fungicial composition according to claim 3, wherein said active agent is a component in a seed treatment solution.

5. The fungicidal composition according to claim 3, wherein said active agent is a component in an emulsion concentrate.

6. The fungicidal composition according to claim 5, wherein said emulsion concentrate contains 15-50% by weight of said active agent and 2-25% by weight of a dispersing agent in a solvent selected from the group consisting of an organic solvent water and a combination thereof.

7. The fungicidal composition according to claim 6, wherein said organic solvent is selected from the group consisting of ethanol, a butanol, dimethylformamide, dimethylsulfoxide, N-methyl-pyrrolidine, an aromatic and a combination thereof.

8. The fungicidal composition according to claim 6, wherein said dispersing agent is selected from the group consisting of an alkyl sulfonate, an aryl sulfonate, carboxymethyl cellulose, a polymer sulfonic acid, a salt of a polymer sulfonic acid, a polyalcohol, a fatty acid ester, a fatty alcohol ether, a fatty amine and a combination thereof.

9. The fungicidal composition according to claim 3, wherein said active agent is a component in a spraying powder.

10. The fungicidal composition according to claim 9, wherein said spraying powder contains 15-70% by weight of said active agent and 1-10% by weight of a dispersing agent.

11. The fungicidal composition according to claim 10, wherein said dispersing agent is selected from the group consisting of a alkyl sulfonate, anaryl sulfonate, carboxymethyl cellulose, a polymer sulfonic acid, a salt of a polymer sulfonic acid, a polyalcohol, a fatty acid ester, a fatty alcohol ether, a fatty amine, and a combination thereof.

12. The fungicidal composition according to claim 3, wherein said active agent is a component in a granulate mixture.

13. The fungicidal composition according to claim 12, wherein said granulate mixture contains 5-10% by weight of said active agent.

14. The fungicidal composition according to claim 3, wherein said active agent is a component in a dusting agent.

15. The fungicidal composition according to claim 14, wherein said dusting agent contains 5-10% by weight of said active agent.

* * * * *